United States Patent
Lee (10) Patent No.: US 8,965,086 B2
(45) Date of Patent: Feb. 24, 2015

(54) SYSTEM AND METHOD FOR PROCESSING IMAGES

(71) Applicant: The University of Western Ontario, London (CA)

(72) Inventor: Ting Yim Lee, London (CA)

(73) Assignee: The University of Western Ontario, London, Ontario (CA)

( * ) Notice: Subject to any disclaimer, the term of this patent is extended or adjusted under 35 U.S.C. 154(b) by 0 days.

(21) Appl. No.: 14/039,619

(22) Filed: Sep. 27, 2013

(65) Prior Publication Data

US 2014/0044334 A1    Feb. 13, 2014

Related U.S. Application Data

(63) Continuation of application No. 13/122,379, filed as application No. PCT/CA2009/001397 on Oct. 2, 2009, now abandoned.

(60) Provisional application No. 61/102,206, filed on Oct. 2, 2008.

(51) Int. Cl.
| | |
|---|---|
| *G06K 9/00* | (2006.01) |
| *G06K 9/40* | (2006.01) |
| *G06T 7/00* | (2006.01) |
| *A61B 5/00* | (2006.01) |
| *A61B 6/00* | (2006.01) |
| *A61B 6/03* | (2006.01) |

(52) U.S. Cl.
CPC .............. *A61B 5/0033* (2013.01); *G06T 7/0016* (2013.01); *A61B 6/037* (2013.01); *G06T 2207/10081* (2013.01); *A61B 6/507* (2013.01); *A61B 6/481* (2013.01); *A61B 6/5258* (2013.01); *A61B 6/504* (2013.01); *A61B 6/486* (2013.01)
USPC ............................ 382/128; 382/254; 382/264

(58) Field of Classification Search
USPC .......................................... 382/103, 128–134
See application file for complete search history.

(56) References Cited

U.S. PATENT DOCUMENTS

| | | | |
|---|---|---|---|
| 6,045,775 A | 4/2000 | Ericcson et al. | |
| 7,187,794 B2 | 3/2007 | Liang et al. | |
| 7,295,692 B2 * | 11/2007 | Nay et al. ....................... | 382/131 |
| 7,831,065 B2 * | 11/2010 | Zimmermann et al. ...... | 382/107 |
| 2003/0160612 A1 | 8/2003 | Yablonskiy et al. | |
| 2004/0005083 A1 * | 1/2004 | Fujimura et al. .............. | 382/103 |
| 2004/0101156 A1 | 5/2004 | Kacker | |
| 2004/0167395 A1 * | 8/2004 | Behrenbruch et al. ........ | 600/420 |
| 2004/0218794 A1 | 11/2004 | Kao et al. | |

(Continued)

FOREIGN PATENT DOCUMENTS

| | | |
|---|---|---|
| WO | 0057777 A1 | 10/2000 |
| WO | 2005120353 | 12/2005 |

OTHER PUBLICATIONS

European Search Report, dated Oct. 18, 2013 (10 pages).

(Continued)

*Primary Examiner* — Alex Liew
(74) *Attorney, Agent, or Firm* — Richard S. Wesorick; Tarolli, Sundheim, Covell & Tummino LLP (57) ABSTRACT

A method of processing a plurality of time separated images comprises selecting a plurality of imaging units in each image; measuring a temporal difference in each imaging unit; and selecting temporal differences above a threshold limit.

26 Claims, 5 Drawing Sheets

(56) References Cited

U.S. PATENT DOCUMENTS

| | | | |
|---|---|---|---|
| 2005/0113680 | A1 | 5/2005 | Ikeda et al. |
| 2005/0286768 | A1 | 12/2005 | Battle |
| 2006/0083407 | A1* | 4/2006 | Zimmermann et al. ...... 382/107 |
| 2007/0183629 | A1* | 8/2007 | Porikli et al. ............... 382/103 |
| 2008/0100472 | A1 | 5/2008 | Mizusawa et al. |
| 2008/0100473 | A1* | 5/2008 | Gao et al. ..................... 340/937 |
| 2008/0146897 | A1* | 6/2008 | Alfano et al. ................ 600/310 |

OTHER PUBLICATIONS

Chinese Office Action dated Mar. 26, 2013 (6 pages).

Razifar et al., "A New Application of Pre-Normalized Principal Component Analysis for Improvement of Image Quality and Clinical Diagnosis in Human Brain Pet Studies—Clinical Brain Studies using [11C]-GR205171, [11C]-L-deuterium-deprenyl, [11C]-5-Hydroxy-L-Tryptophan, [11C]-L-DOPA and Pittsburgh Compound-B" NeuroImage, vol. 33, No. 2, 2008, pp. 588-598.

Balasubramanian et al., "Adaptive Noise Filtering of White-Light Confocal Microscope Images Using Karhunen-Loeve Expansion" Proc. Of SPIE, vol. 5909, 2005, pp. 590904-1-590904-12.

Pedersen et al., "Prinicpal Component Analysis of Dynamic PET and Gamma Camera Images: A Methodology to Visualize the Signals in the Presence of Large Noise" Nuclear Science Symposium and Medical Conference Record, San Francisco, CA, 1993, pp. 1734-1738.

Hua et al., "Mosiac Alogrithm of Video Sequence", Journal of Computer Applications, vol. 27, No. 11, 2007, 1 page.

Chinese Office Action dated Jun. 18, 2014, (17 pages).

Wang, "PCA Method Used in Image Fusion", Microcomputer Information, 2007, pp. 285-287.

* cited by examiner

SYSTEM AND METHOD FOR PROCESSING IMAGES

CROSS-REFERENCE TO RELATED APPLICATIONS

This application is a continuation of U.S. patent application Ser. No. 13/122,379 to Lee filed on Apr. 1, 2011 and entitled "SYSTEM AND METHOD FOR PROCESSING IMAGES", which is a national stage of PCT/CA2009/001397 filed on Oct. 2, 2009, entitled "SYSTEM AND METHOD FOR PROCESSING IMAGES", which claims the benefit of U.S. Provisional Application No. 61/102,206 to Lee filed on Oct. 2, 2008 and entitled "SYSTEM AND METHOD FOR PROCESSING IMAGES", the content of which is incorporated herein by reference.

FIELD OF THE INVENTION

The present invention relates generally to image processing and, more particularly, to a system and method for processing image data obtained by using a dynamic imaging technique

BACKGROUND OF THE INVENTION

Medical imaging encompasses techniques and processes used to create images of the human body for clinical purposes, including medical procedures for diagnosing or monitoring disease. Medical imaging technology has grown to encompass many image recording techniques including electron microscopy, fluoroscopy, magnetic resonance imaging (MRI), nuclear medicine, photoacoustic imaging, positron emission tomography (PET), projection radiography, thermography, computed tomography (CT), and ultrasound.

Medical imaging can incorporate the use of compounds referred to as contrast agents or contrast materials to improve the visibility of internal bodily structures in an image.

Medical imaging was originally restricted to acquisition of singular static images to capture the anatomy of an organ/region of the body. Currently, the use of more sophisticated imaging techniques allows dynamic studies to be made that provide a temporal sequence of images which can characterize physiological or pathophysiological information.

Dynamic medical imaging involves an acquisition process that takes many "snapshots" of the organ/region/body of interest over time in order to capture a time-varying behaviour, for example, distribution of a contrast agent and hence capture of a specific biological state (disease, condition, physiological phenomenon, etc.). As the speed and digital nature of medical imaging evolves, this acquisition data can have tremendous temporal resolution and can result in large quantities of data.

Medical imaging technologies have been used widely to improve diagnosis and care for such conditions as cancer, heart disease, brain disorders, and cardiovascular conditions. Most estimates conclude that millions of lives have been saved or dramatically improved as a result of these medical imaging technologies. However, the risk of radiation exposure from such medical imaging technologies for patients must be considered.

In this regard, the increasing use of CT in medical diagnosis has highlighted concern about the increased cancer risk to exposed patients because of the larger radiation doses delivered in CT than the more common, conventional x-ray imaging procedures. This is particularly true with the two-phase CT Perfusion protocol. For illustration purposes, using the dose-length product for a protocol provided by a commercially available CT scanner (GE Healthcare), the effective dose of a CT Stroke series consisting of: 1) a non-enhanced CT scan to rule out hemorrhage; 2) a CT angiography to localize the occlusion causing the stroke; and 3) a two-phase CT Perfusion protocol to define the ischemic region with blood flow and blood volume and predict hemorrhagic transformation (HT) with blood-brain barrier permeability surface area product (BBB-PS); is 10 mSv, of which 4.9 mSv is contributed by the two-phase CT Perfusion protocol. The CT Stroke series is predicted to induce 80 and 131 additional cancers for every exposed 100,000 male and female acute ischemic stroke (AIS) patients, respectively, with the two-phase CT Perfusion protocol alone predicted to cause half of the additional cancers (Health Risks from Exposure to Low Levels of Ionizing Radiation: BEIR VII. The National Academies Press, Washington D.C., 2006).

Unless the effective dose of the two-phase CT Perfusion protocol is reduced, the benefits of medical imaging will be undermined by the concern over cancer induction. Furthermore, the concern over the risks of radiation exposure extends to other medical imaging techniques, particularly for pediatric patients or those patients undergoing repeated exposure.

The use of statistical filtering techniques to increase the signal to noise ratio in low dose radiation imaging has been described, for example in U.S. Pat. No. 7,187,794 issued Mar. 6, 2007. However, at present the application of statistical filtering is limited to projection data prior to the construction of images. Several disadvantages are associated with statistical filtering of projection data. For example, the computational burden when working with projection data is high because each image from a dynamic sequence is typically reconstructed from ~1,000 projections. In addition, the filtering process has to be 'hardwired' into the image reconstruction pipeline of the scanner. As such, statistical filters of projection data lack flexibility as they are typically specific to a scanner platform.

Whether perceived or proven, concerns over the risk of radiation exposure will have to be addressed to assure patients of the long term safety of medical imaging techniques. Accordingly, there is a need for medical imaging techniques that allow for a reduction in radiation dose.

It is therefore an object of the present invention to provide a novel system and method for processing images.

SUMMARY OF THE INVENTION

In an aspect, there is provided a method of processing a plurality of time separated images comprising: selecting a plurality of imaging units in each image; determining a temporal difference for each imaging unit; and selecting temporal differences above a threshold limit.

In another aspect, there is provided a system for processing a plurality of time separated images comprising: an interface for receiving a plurality of time separated images; and a processor for selecting a plurality of imaging units in each image, determining a temporal difference for each imaging unit, and selecting temporal differences above a threshold limit.

In yet another aspect, there is provided a computer readable medium embodying a computer program for processing a plurality of time separated images, the computer program comprising: computer program code for selecting a plurality of imaging units in each image; computer program code for determining a temporal difference for each imaging unit; and computer program code for selecting temporal differences above a threshold limit.

BRIEF DESCRIPTION OF THE DRAWINGS

Embodiments will now be described, by way of example only, with reference to accompanying drawings in which.

DETAILED DESCRIPTION

Dynamic medical imaging involves an acquisition process that takes many "snapshots" of an organ/region/body of interest (i.e. a target region) over time in order to capture a time-varying behaviour, for example uptake and/or wash out of a contrast agent. This acquisition process results in the production of a plurality of time separated images. The method and system described herein involves processing of such time separated images.

Figure 1:
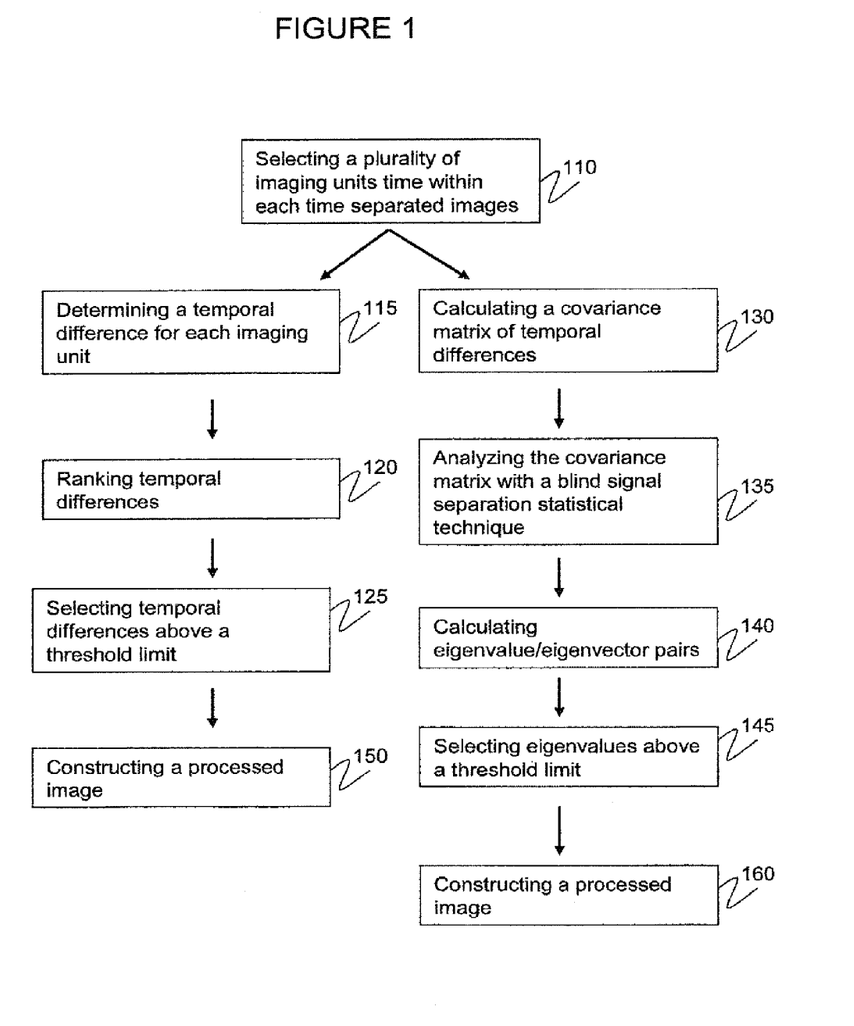
FIG. 1 is a flow chart of an image processing method.

Turning now to FIG. 1, the steps performed during processing of time separated images according to the method are illustrated. The plurality of time separated images may be obtained from dynamic medical imaging of a patient with or without the use of an injected contrast agent. A contrast agent can selectively increase the contrast of the target region in an image, for example on the basis of the target region's structure or physiological state. For example, one may inject into a patient a compound which has a biophysical, molecular, genetic or cellular affinity for a particular organ, disease, state or physiological process. Such contrast agents are selected to have a property that provides enhanced information to a given imaging technique by altering imaging conditions, for example by altering image contrast, to reflect the behaviour of the compound in the body. This may be achieved via increased X-ray attenuation at a localized site (e.g. for CT/X-ray), altered paramagnetic properties (e.g. for MRI) or the use of a radioisotope for nuclear medicine/PET. Contrast agents for many imaging techniques are well-known. In some cases contrast enhancement does not rely on an injected contrast agent, for example the use of "black blood" or "white blood" in magnetic resonance imaging (MRI) where specific pulse sequences are used to change the magnetic saturation of the blood and thus its appearance in the image, or tagged MRI sequences which alter the magnetic behaviour of a particular tissue or fluid. An injected contrast agent, or a tissue or fluid with altered behaviour, may all be regarded as "imaging agents".

The plurality of time separated images are not limited to any particular imaging technique and include, for example, dynamic medical imaging using magnetic resonance imaging (MRI), computed tomography (CT), nuclear medicine (NM) or positron emission tomography (PET). The plurality of time separated images are also not limited to particular image types. For example, grayscale or colour images may be processed.

During the method, within each time separated image a plurality of imaging units are selected (step 110). An "imaging unit" may be any desired unit for separating an image into equivalent portions including, for example, a pixel, a plurality of pixels, a fraction of a pixel, a voxel, a plurality of voxels, a fraction of a voxel etc.

The imaging unit data is represented by a value, for example a digital value, and can thus be quantified and measured. Typically, image intensity is measured for corresponding imaging units in the time separated images. For dynamic imaging using contrast agents a temporal difference can be determined with respect to contrast concentration. The temporal difference of contrast concentration can be represented as a plot of contrast enhancement as a function of time.

Two alternatives for determining temporal differences of contrast concentration and selecting temporal differences are shown in FIG. 1. In one alternative shown in FIG. 1, once the plurality of imaging units has been selected from each time separated image at step 110, a temporal difference is determined for each imaging unit (step 115). The determined temporal difference or representations thereof are then ranked according to degree of observed temporal difference (step 120). Temporal differences above a threshold limit are then selected (step 125). A processed image is then constructed on the basis of the selected temporal differences (step 150).

In the other alternative shown in FIG. 1, the temporal differences are not ranked. Rather, the temporal data for imaging units are analyzed to select temporal differences above a threshold limit using statistical techniques, and more particularly blind signal separation statistical techniques. For example, with respect to dynamic CT imaging using a contrast agent, once the plurality of imaging units have been selected from each time separated image at step 110, a covariance matrix of the co-variations of all pairs of contrast enhancement plots in relation to a mean curve is established (step 130) and analyzed with a blind signal separation statistical technique (step 135), such as with a principal components analysis being applied to the covariance matrix. Eigenvector/eigenvalue pairs are calculated on the basis of the statistical analysis (step 140). Resulting eigenvector/eigenvalue pairs above a threshold limit are then selected on the basis of their eigenvalues (step 145). A processed image is then constructed using the selected eigenvectors, with different weightings of the selected eigenvectors being used to construct individual imaging units (step 160).

The plurality of time separated images may optionally be registered to correlate corresponding locations in the time separated images to each other. Registration of the plurality of time separated images is only needed to correct for gross misregistration. Otherwise, slight movement between the time separated images may be tolerated and may even be removed by the processing method described herein.

As another optional step, the plurality of time separated images may be preprocessed so that the time separated images are represented with quantifiable values or codes. For example, the time separated images may be represented by digital values using known digitization techniques. If the imaging data of the plurality of time separated images is provided in a digital form, then a digitization step is not necessary.

Figure 2:
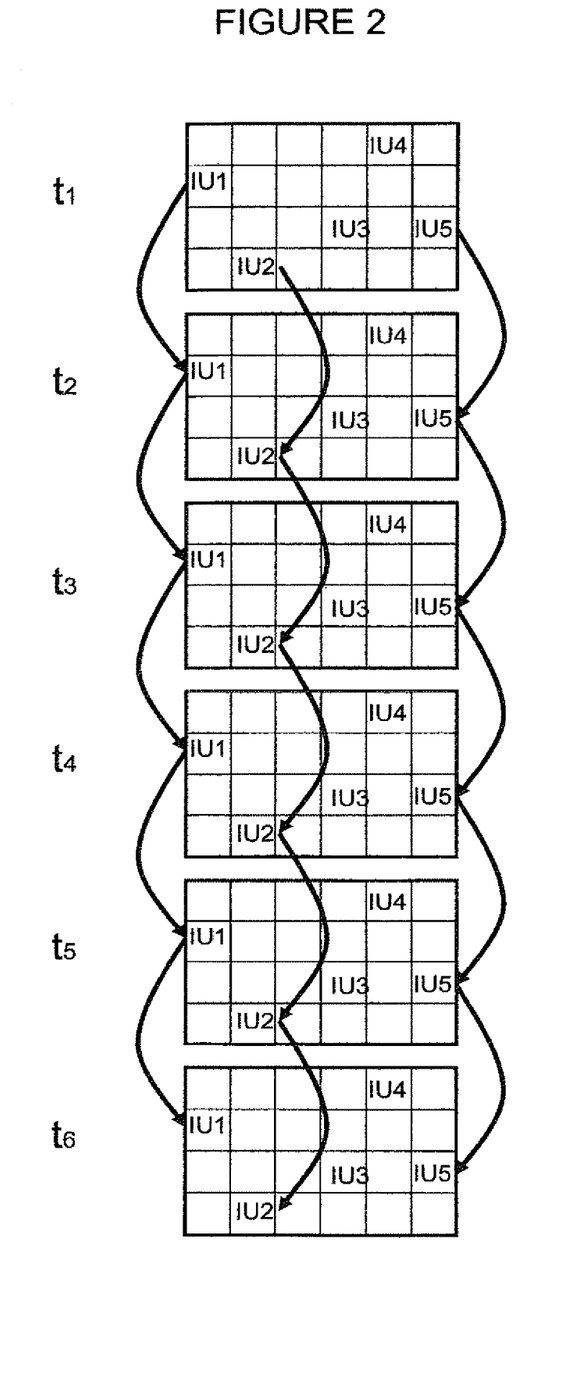
FIG. 2 schematically illustrates the positioning of imaging units in a plurality of time separated images.

The determination of temporal differences of contrast concentration will now be further described with reference to FIG. 2. FIG. 2 shows a series of six chronologically ordered time separated images, $t_1$ to $t_6$. A 4×6 array of imaging units is marked on each time separated image. In this example, five (5) imaging units, IU1 to IU5, have been selected. As is clear from comparing the entire series of time separated images, $t_1$ to $t_6$, imaging unit IU1 is selected at the same position of the array (i.e. column 1, row 2) for each of the time separated images. Similarly, each of imaging units IU2 to IU5 is selected in corresponding positions of the imaging unit array throughout the series of time separated images. Accordingly, values for each imaging unit at its corresponding position throughout the time separated images can be plotted as a function of time to obtain a temporal curve. The plotting step is illustrated by the arrows linking the corresponding positions of imaging units IU1, IU2 and IU5. The temporal curve for each imaging unit can then be analyzed to determine a temporal difference. For example, a mean curve for all of the temporal curves obtained can be calculated. The mean curve is then subtracted from each of the temporal curves to obtain a temporal difference curve for each selected imaging unit. It will be understood, that the marked array and the selection of imaging units IU1 to IU5, as well as the arrows representing plotting of values for imaging units IU1, IU2, and IU5 as a function of time, is for illustration purposes only, and that any number of imaging units may be selected and analyzed as desired. Furthermore, the determination of temporal differences by subtraction of a mean curve from the temporal curves for imaging units is for illustration only, and other methods of analyzing the temporal curves, for example using derivatives and/or statistical techniques are contemplated.

A mathematical basis for blind signal separation statistical analysis of a plurality of time separated images is now provided using time separated images from a CT Perfusion study as an example.

Given a series of n dynamic (i.e. time separated) images from a CT Perfusion study, the n dynamic images can be represented compactly as a matrix:

$$\tilde{X} = [\tilde{x}_1^T \tilde{x}_2^T \ldots \tilde{x}_{p-1}^T \tilde{x}_p^T]^T$$

where p is the number of pixels in a CT image (i.e. p=512× 512, 256×256, etc) and $\tilde{x}_i$, i=1, ..., p is a n×1 vector whose elements are the pixel values in the n images or the time vs. enhancement curve from the $i^{th}$ pixel. Note that the $(i,j)^{th}$ element of $\tilde{X}$ is the $j^{th}$ element $x_{ij}$ of $\tilde{x}_i$. Each $\tilde{x}_i$, i=1, ..., p can also be interpreted as repeated observations of a single time vs. enhancement curve $\chi$ (a random process consisting of n random variables, $\chi_1, \chi_2, \ldots, \chi_{n-1}, \chi_n$).

Notation is interpreted as follows:
(i) a vector is represented by a tilde above a Greek or Roman alphabet character with elements arranged in a column;
(ii) a matrix is represented by tilde over a capitalized Greek or Roman alphabet character;
(iii) the transpose of a vector or a matrix is indicated by a superscript T on the symbol; and
(iv) a random variable is represented by a Greek alphabet character while an observation (samples) of a random variable is represented by the corresponding Roman alphabet character; the correspondence between Greek and Roman alphabet character will be used as shown below in the following discussion:

$$\chi \leftrightarrow x$$

$$\psi \leftrightarrow y$$

$$\zeta \leftrightarrow z$$

(v) a random process consisting of n random variables is represented by a n×1 vector.

One approach to removing noise from the n dynamic images is to find an 'expansion' of the p×n matrix, $\tilde{X}$ and then truncate the expansion by certain pre-determined criteria. A common expansion is the singular value decomposition of $\tilde{X}$:

$$\tilde{X} = \tilde{U} \cdot \tilde{L} \cdot \tilde{V}^T \quad (1)$$

where $\tilde{U}$ is a p×p orthogonal matrix, $\tilde{V}$ is a n×n orthogonal matrix, and $\tilde{L}$ is a p×n diagonal matrix with singular values of $\tilde{X}$ as its diagonal elements. Let $l_1, \ldots, l_n$ be the singular values of $\tilde{X}$ (it is assumed without loss of generality that $\tilde{X}$ is of full column rank, n and p>n). Then:

$$\tilde{L} = [\tilde{l}_1 \ldots \tilde{l}_n]$$

where $\tilde{l}_i$, i=1, ..., n is a p×1 vector with zero elements except for the $i^{th}$ element which is $l_i$. Usually the singular values $l_1, \ldots, l_n$ are arranged in descending order and small singular values can be discarded as arising from noise. A simple way to reduce noise in $\tilde{X}$ is to keep only r<n singular values. Then:

$$\tilde{L} = [\tilde{l}_1 \ldots \tilde{l}_r \tilde{0}_{r+1} \ldots \tilde{0}_n]$$

If the truncated series of singular values is used to reconstitute $\tilde{X}$ according to Equation (1), then:

$$\tilde{X} \approx [\tilde{u}_1 \; \tilde{u}_2 \; \ldots \; \tilde{u}_p] \cdot [\tilde{l}_1 \; \ldots \; \tilde{l}_r \; \tilde{0}_{r+1} \; \ldots \; \tilde{0}_n] \cdot \begin{bmatrix} \tilde{v}_1^T \\ \vdots \\ \tilde{v}_r^T \\ \tilde{v}_{r+1}^T \\ \vdots \\ \tilde{v}_n^T \end{bmatrix}$$

where $\tilde{u}_i$, i=1, ..., p is the $i^{th}$ column of $\tilde{U}$ and $\tilde{v}_i$, i=1, ..., n is the $i^{th}$ column of $\tilde{V}$. Evaluating the expansion, yields:

$$\tilde{X} \approx [\tilde{u}_1 \; \tilde{u}_2 \; \ldots \; \tilde{u}_p] \cdot [\tilde{l}_1 \; \ldots \; \tilde{l}_r \; \tilde{0}_{r+1} \; \ldots \; \tilde{0}_n] \cdot \begin{bmatrix} \tilde{v}_1^T \\ \vdots \\ \tilde{v}_r^T \\ \tilde{v}_{r+1}^T \\ \vdots \\ \tilde{v}_n^T \end{bmatrix} \quad (2)$$

$$\approx [\tilde{u}_1 \; \tilde{u}_2 \; \ldots \; \tilde{u}_p] \cdot [\tilde{l}_1 \cdot \tilde{v}_1^T + \ldots + \tilde{l}_r \cdot \tilde{v}_r^T]$$

$$\approx [\tilde{u}_1 \; \tilde{u}_2 \; \ldots \; \tilde{u}_p] \cdot \left( \begin{bmatrix} l_1 \\ \vdots \\ 0_r \\ 0_{r+1} \\ \vdots \\ 0_p \end{bmatrix} \cdot \tilde{v}_1^T + \ldots + \begin{bmatrix} 0 \\ \vdots \\ l_r \\ 0_{r+1} \\ \vdots \\ 0_p \end{bmatrix} \cdot \tilde{v}_r^T \right)$$

$$\approx [\tilde{u}_1 \; \tilde{u}_2 \; \ldots \; \tilde{u}_p] \cdot \begin{bmatrix} l_1 \cdot \tilde{v}_1^T \\ \vdots \\ l_r \cdot \tilde{v}_r^T \\ 0_{r+1} \\ \vdots \\ 0_p \end{bmatrix}$$

$$= \sum_{i=1}^{r} l_i \cdot \tilde{u}_i \cdot \tilde{v}_i^T$$

Thus, in the expansion of $\tilde{X}$, keeping r singular values means that only the first r columns of $\tilde{U}$ and $\tilde{V}$ is needed.

The singular value decomposition (SVD) (expansion) of $\tilde{X}$ as formulated here, however, has two main disadvantages in de-noising dynamic images from CT Perfusion, namely:
1. The size of the matrix $\tilde{X}$ can be as large as $(256)^2 \times 40\text{-}60$, making it computationally prohibitive to find the SVD of $\tilde{X}$; and 2. Although the criterion of discarding small singular values makes general sense, it is difficult to justify the threshold used to keep or discard singular values.

An alternative method to achieve the SVD of $\tilde{X}$ will now be described. As stated above, the time vs. enhancement curves from each pixel (or pixel block) $\tilde{x}_i$, i=1, . . . , p can be regarded as repeated samples (observations) of the underlying random process (time vs. enhancement curve). $\chi$. Then the sample mean of the random process, $\bar{x}$, can be calculated as:

$$\bar{x} = \frac{1}{p} \cdot \sum_{i=1}^{p} \tilde{x}_i \quad (3)$$

$\bar{x}$ by definition is a n×1 vector (the sample mean time vs. enhancement curve) and the $j^{th}$ component of $\bar{x}$, according to Equation (3), is:

$$\bar{x}_j = \frac{1}{p} \cdot \sum_{i=1}^{p} \tilde{x}_{ij}$$

where $\tilde{x}_{ij}$ is the $j^{th}$ component of $\tilde{x}_i$

The zero mean random process from is $\tilde{\chi}$ is $\tilde{\psi}=\chi-\bar{\chi}$, where $\bar{\chi}$ is the population mean of $\chi$. For each observation (sample) $\tilde{x}_i$ of $\tilde{\chi}$, the corresponding observation (sample) of $\tilde{\psi}$ is given by:

$$\tilde{y}_i = \tilde{x}_i - \bar{x}.$$

The sample mean of $\tilde{\psi}$, $\bar{y}$, a n×1 vector is given by:

$$\bar{y} = \frac{1}{p} \cdot \sum_{i=1}^{p} \tilde{y}_i = \frac{1}{p} \cdot \sum_{i=1}^{p} (\tilde{x}_i - \bar{x}) = \left(\frac{1}{p} \cdot \sum_{i=1}^{p} \tilde{x}_i\right) - \bar{x} = \tilde{0}$$

where $\tilde{0}$ is a n×1 zero vector as expected since $\tilde{\psi}$ is a zero mean random process.

Let $\tilde{Y}=[\tilde{y}_1^T \tilde{y}_2^T \ldots \tilde{y}_{p-1}^T \tilde{y}_p^T]^T$ be a p×n matrix whose rows are $\tilde{y}_i^T$ i=1, . . . , p. Then:

$$\tilde{Y}^T \cdot \tilde{Y} = [\tilde{y}_1 \quad \tilde{y}_2 \quad \ldots \quad \ldots \quad \tilde{y}_{p-1} \quad \tilde{y}_p] \cdot \begin{bmatrix} \tilde{y}_1^T \\ \tilde{y}_2^T \\ \vdots \\ \vdots \\ \tilde{y}_{p-1}^T \\ \tilde{y}_p^T \end{bmatrix} \quad (4)$$

$$= \sum_{i=1}^{p} \tilde{y}_i \cdot \tilde{y}_i^T$$

$$= \sum_{i=1}^{p} \begin{bmatrix} \tilde{y}_{i1}^2 & \tilde{y}_{i1} \cdot \tilde{y}_{i2} & \ldots & \ldots & \tilde{y}_{i1} \cdot \tilde{y}_{in-1} & \tilde{y}_{i1} \cdot \tilde{y}_{in} \\ \tilde{y}_{i2} \cdot \tilde{y}_{i1} & \tilde{y}_{i2}^2 & \ldots & \ldots & \tilde{y}_{i2} \cdot \tilde{y}_{in-1} & \tilde{y}_{i2} \cdot \tilde{y}_{in} \\ \vdots & \vdots & \vdots & \vdots & \vdots & \vdots \\ \vdots & \vdots & \vdots & \vdots & \vdots & \vdots \\ \tilde{y}_{in-1} \cdot \tilde{y}_{i1} & \tilde{y}_{in-1} \cdot \tilde{y}_{i2} & & & \tilde{y}_{in-1}^2 & \tilde{y}_{in-1} \cdot \tilde{y}_{in} \\ \tilde{y}_{in} \cdot \tilde{y}_{i1} & \tilde{y}_{in} \cdot \tilde{y}_{i2} & & & \tilde{y}_{in} \cdot \tilde{y}_{in-1} & \tilde{y}_{in}^2 \end{bmatrix}$$

-continued $$= \begin{bmatrix} \sigma_1^2 & \sigma_{12}^2 & \ldots & \ldots & \sigma_{1n-1}^2 & \sigma_{1n}^2 \\ \sigma_{21}^2 & \sigma_2^2 & \ldots & \ldots & \sigma_{2p-1}^2 & \sigma_{2n}^2 \\ \vdots & \vdots & \vdots & \vdots & \vdots & \vdots \\ \vdots & \vdots & \vdots & \vdots & \vdots & \vdots \\ \sigma_{n-11}^2 & \sigma_{n-12}^2 & \ldots & \ldots & \sigma_{n-1}^2 & \sigma_{n-1n}^2 \\ \sigma_{n1}^2 & \sigma_{n2}^2 & \ldots & \ldots & \sigma_{nn-1}^2 & \sigma_n^2 \end{bmatrix}$$

where $\sigma_i^2$ is the sample variance of $\psi_i$ i=1, . . . , n and $\sigma_{ij}^2$ is the sample covariance of and $\psi_i$ and $\psi_j$ i,j=1, . . . , n.

Or, $$\tilde{S} = \frac{1}{p-1} \cdot \tilde{Y}^T \cdot \tilde{Y}$$

is the sample covariance matrix of $\tilde{\psi}$ and is of dimension n×n. In CT Perfusion n is typically 40-60.

A linear combination of $\psi_i$, i=1, . . . , n, $\zeta$, can be defined as:

$$\zeta = \tilde{a}^T \cdot \tilde{\psi}$$

where $\tilde{a}$ is a given n×1 vector of coefficients. $\zeta$ is a random variable (not process) with observations $z_i$ i=1, . . . , p given by:

$$z_i = \tilde{a}^T \cdot \tilde{y}_i$$

by definition of $\zeta$. The sample mean of $\zeta$, $\bar{z}$, is given by:

$$\bar{z} = \frac{1}{p} \cdot \sum_{i=1}^{p} \tilde{z}_i = \frac{1}{p} \cdot \sum_{i=1}^{p} \tilde{a}^T \cdot \tilde{y}_i = \tilde{a}^T \cdot \frac{1}{p} \cdot \sum_{i=1}^{p} \tilde{y}_i = 0$$

Thus, $\zeta$ is also a zero mean random variable. The sample variance of $\zeta$ is given by:

$$\text{sample var}(\zeta) = \frac{1}{p-1} \cdot \sum_{i=1}^{p} (z_i)^2$$

$$= \frac{1}{p-1} \cdot \sum_{i=1}^{p} (\tilde{a}^T \cdot \tilde{y}_i) \cdot (\tilde{a}^T \cdot \tilde{y}_i)^T$$

$$= \frac{1}{p-1} \cdot \sum_{i=1}^{p} \tilde{a}^T \cdot \tilde{y}_i \cdot \tilde{y}_i^T \cdot \tilde{a}$$

$$= \frac{1}{p-1} \cdot \tilde{a}^T \cdot \left(\sum_{i=1}^{p} \tilde{y}_i \cdot \tilde{y}_i^T\right) \cdot \tilde{a}$$

$$= \tilde{a}^T \cdot \tilde{S} \cdot \tilde{a}$$

Determination of the vector of coefficients, $\tilde{a}$, to maximize the sample variance of $\zeta$, $\tilde{a}^T \cdot \tilde{S} \cdot \tilde{a}$ a will now be investigated. Since $\tilde{a}^T \cdot \tilde{S} \cdot \tilde{a}$ can be made as large as required by scaling $\tilde{a}$ with a constant, the optimization can only be done by imposing a normalization condition, such as $\tilde{a}^T \cdot \tilde{a} = 1$. To maximize $\tilde{a}^T \cdot \tilde{S} \cdot \tilde{a}$ subject to $\tilde{a}^T \cdot \tilde{a} = 1$, the standard approach is to use the technique of Lagrange multipliers. That is it is sought to maximize:

$$\tilde{a}^T \cdot \tilde{S} \cdot \tilde{a} - \lambda \cdot (\tilde{a}^T \cdot \tilde{a} - 1)$$

where $\lambda$ is the Lagrange multiplier. Differentiation with respect to $\tilde{a}$ gives:

$$\tilde{S} \cdot \tilde{a} - \lambda \cdot \tilde{a} = \tilde{0}$$

Thus, $\lambda$ is the eigenvalue of $\tilde{S}$ and $\tilde{a}$ is the corresponding eigenvector and sample var($\zeta$)=$\tilde{a}^T \cdot \tilde{S} \cdot \tilde{a}$=$\tilde{a}^T \cdot \lambda \cdot \tilde{a}$=$\lambda$, the eigenvalue of $\tilde{S}$ That is to maximize $\tilde{a}^T \cdot \tilde{S} \cdot \tilde{a}$ subject to $\tilde{a}^T \cdot \tilde{a}$=1, $\tilde{a}$ is the eigenvector of $\tilde{S}$ that has the highest eigenvalue.

Let $\lambda_1$ be the largest eigenvalue with the corresponding eigenvector $\tilde{a}_1$, then $\zeta_1 = \tilde{a}_1^T \cdot \psi$ is called the first sample principal component of $\psi$. It is a random variable with observations defined by $z_{i1} = \tilde{a}_1^T \cdot \tilde{y}_i$, $z_{i1}$ is also called the score of the $i^{th}$ observation on the first principal component. The second principal component, $\zeta_2 = \tilde{a}_2^T \cdot \psi$, similarly, maximizes the sample variance of $\zeta_2$, $\tilde{a}_2^T \cdot \tilde{S} \cdot \tilde{a}_2$, subject to being uncorrelated to $\zeta_1$ and the normalization conditional $\tilde{a}_2^T \cdot \tilde{a}_2$=1. The observations corresponding to $\zeta_2$ is $z_{i2} = \tilde{a}_2^T \cdot \tilde{y}_i$. The sample covariance of $\zeta_1$ and $\zeta_2$ is:

$$\text{sample cov}(\zeta_1, \zeta_2) = \frac{1}{p-1} \cdot \sum_{i=1}^{p} z_{i1} \cdot z_{i2}$$

$$= \frac{1}{p-1} \cdot \sum_{i=1}^{p} (\tilde{a}_1^T \cdot \tilde{y}_i) \cdot (\tilde{a}_2^T \cdot \tilde{y}_i)^T$$

$$= \frac{1}{p-1} \cdot \sum_{i=1}^{p} \tilde{a}_1^T \cdot \tilde{y}_i \cdot \tilde{y}_i^T \cdot \tilde{a}_2$$

$$= \frac{1}{p-1} \cdot \tilde{a}_1^T \cdot \left( \sum_{i=1}^{p} \cdot \tilde{y}_i \cdot \tilde{y}_i^T \right) \cdot \tilde{a}_2$$

$$= \tilde{a}_1^T \cdot \tilde{S} \cdot \tilde{a}_2$$

$$= \frac{1}{p-1} \cdot \sum_{i=1}^{p} (\tilde{a}_2^T \cdot \tilde{y}_i) \cdot (\tilde{a}_1^T \cdot \tilde{y}_i)^T$$

$$= \tilde{a}_2^T \cdot \tilde{S} \cdot \tilde{a}_1$$

The requirement that $\zeta_2$ is uncorrelated to $\zeta_1$ is the same as requiring:

$\tilde{a}_2^T \cdot \tilde{S} \cdot \tilde{a}_1 = \tilde{a}_2^T \cdot \lambda_1 \cdot \tilde{a}_1 = \lambda_1 \cdot [\tilde{a}_2^T \cdot \tilde{a}_1] = 0 \Rightarrow \tilde{a}_2^T \cdot \tilde{S} \cdot \tilde{a}_1 = 0$ and
$\tilde{a}_2^T \cdot \tilde{a}_1 = 0$ $\tilde{a}_1^T \cdot \tilde{S} \cdot \tilde{a}_2 = (\tilde{S} \cdot \tilde{a}_1)^T \cdot \tilde{a}_2 = \lambda_1 \cdot [\tilde{a}_1^T \cdot \tilde{a}_2] = 0 \Rightarrow \tilde{a}_1^T \cdot \tilde{S} \cdot \tilde{a}_2 = 0$ and
$\tilde{a}_1^T \cdot \tilde{a}_2 = 0$ Thus, any of the conditions:

$\tilde{a}_2^T \cdot \tilde{S} \cdot \tilde{a}_1 = 0$ $\tilde{a}_2^T \cdot \tilde{a}_1 = 0$ $\tilde{a}_1^T \cdot \tilde{S} \cdot \tilde{a}_2 = 0$ $\tilde{a}_1^T \cdot \tilde{a}_2 = 0$ can be used to specify that $\zeta_2$ is uncorrelated to $\zeta_1$.

To maximize the sample variance of $\zeta_2$, $\tilde{a}_2^T \cdot \tilde{S} \cdot \tilde{a}_2$, subject to the conditions that $\zeta_2$ is uncorrelated to $\zeta_1$ and $\tilde{a}_2^T \cdot \tilde{a}_2 = 1$ is the same as to maximize:

$\tilde{a}_2^T \cdot \tilde{S} \cdot \tilde{a}_2 - \lambda_2 \cdot (\tilde{a}_2^T \cdot \tilde{a}_2 - 1) - \phi \tilde{a}_2^T \cdot \tilde{a}_1$ where the condition $\tilde{a}_2^T \cdot \tilde{a}_1 = 0$ is used to specify that $\zeta_2$ is uncorrelated to $\zeta_1$ and $\lambda_2$ and $\phi$ are Lagrange multipliers. Differentiation with respect to $\tilde{a}_2$ gives:

$\tilde{S} \cdot \tilde{a}_2 - \lambda_2 \cdot \tilde{a}_2 - \phi \cdot \tilde{a}_1 = 0$ Multiplying through by $\tilde{a}_1^T$ gives:

$\tilde{a}_1^T \cdot \tilde{S} \cdot \tilde{a}_2 - \lambda_2 \cdot \tilde{a}_1^T \cdot \tilde{a}_2 - \phi \cdot \tilde{a}_1^T \cdot \tilde{a}_1 = 0$ which, since the first two terms are zero and $\tilde{a}_1^T \cdot \tilde{a}_1 = 1$, reduces to $\phi = 0$. Therefore, $\tilde{S} \cdot \tilde{a}_2 - \lambda_2 \cdot \tilde{a}_2 = 0$ so $\lambda_2$ is once more an eigenvalue of $\tilde{S}$, and $\tilde{a}_2$ the corresponding eigenvector.

Again, $\tilde{a}_2^T \cdot \tilde{S} \cdot \tilde{a}_2 = \lambda_2$ or the sample variance of $\zeta_2$ is $\lambda_2$. Assuming that $\tilde{S}$ does not have repeat eigenvalues, $\lambda_2$ cannot be equal to $\lambda_1$. If it did, it follows that $\tilde{a}_2 = \tilde{a}_1$, violating the constraint that $\tilde{a}_2^T \cdot \tilde{a}_1 = 0$. Hence $\lambda_2$ is the second largest eigenvalue and $\tilde{a}_2$ the corresponding eigenvector.

It can be shown using the same technique that for the third, fourth, ..., $n^{th}$ sample principal components, the vectors of coefficients $\tilde{a}_3, \tilde{a}_4, \ldots, \tilde{a}_n$ are the eigenvectors of $\tilde{S}$ corresponding to $\lambda_3, \lambda_4, \ldots, \lambda_n$, the third, fourth largest, ..., and the smallest eigenvalue. Furthermore, the sample variances of the principal components are also given by the eigenvalues of $\tilde{S}$.

Define $\tilde{Z}$ to be the p×n matrix of the scores of observations on principal components. In this case, the $i^{th}$ row consists of the scores of the $i^{th}$ observation of $\tilde{\psi}$ (i.e. $\tilde{y}_i$) on all principal components $\zeta_1, \zeta_2, \ldots, \zeta_{n-1}, \zeta_n$, that is:

$$\tilde{Z} = \begin{bmatrix} \tilde{a}_1^T \cdot \tilde{y}_1 & \ldots & \tilde{a}_j^T \cdot \tilde{y}_1 & \ldots & \tilde{a}_n^T \cdot \tilde{y}_1 \\ \vdots & \ddots & \vdots & \ddots & \vdots \\ \tilde{a}_1^T \cdot \tilde{y}_i & \ldots & \tilde{a}_j^T \cdot \tilde{y}_i & \ldots & \tilde{a}_n^T \cdot \tilde{y}_i \\ \vdots & \ddots & \vdots & \ddots & \vdots \\ \tilde{a}_1^T \cdot \tilde{y}_p & \ldots & \tilde{a}_j^T \cdot \tilde{y}_p & \ldots & \tilde{a}_n^T \cdot \tilde{y}_p \end{bmatrix} \quad (4a)$$

$$= \begin{bmatrix} \tilde{a}_1^T \cdot \tilde{y}_1 & \ldots & \tilde{a}_1^T \cdot \tilde{y}_i & \ldots & \tilde{a}_1^T \cdot \tilde{y}_p \\ \vdots & \ddots & \vdots & \ddots & \vdots \\ \tilde{a}_j^T \cdot \tilde{y}_1 & \ldots & \tilde{a}_j^T \cdot \tilde{y}_i & \ldots & \tilde{a}_j^T \cdot \tilde{y}_p \\ \vdots & \ddots & \vdots & \ddots & \vdots \\ \tilde{a}_n^T \cdot \tilde{y}_1 & \ldots & \tilde{a}_n^T \cdot \tilde{y}_i & \ldots & \tilde{a}_n^T \cdot \tilde{y}_p \end{bmatrix}^T$$

$$= \left( \begin{bmatrix} \tilde{a}_1^T \\ \tilde{a}_j^T \\ \tilde{a}_n^T \end{bmatrix} \cdot [\tilde{y}_1 \ldots \tilde{y}_i \ldots \tilde{y}_p] \right)^T$$

$$= [\tilde{y}_1^T \ldots \tilde{y}_i^T \ldots \tilde{y}_{p_p}^T]^T \cdot [\tilde{a}_1 \ldots \tilde{a}_j \ldots \tilde{a}_n]$$

$$= \tilde{Y} \cdot \tilde{A}$$

where $\tilde{A}$ is a n×n matrix whose columns are the eigenvectors of $\tilde{S}$ and is orthogonal.

The first principal component, $\zeta_1$, maximized is expressed by:

$$\tilde{a}_1^T \cdot \tilde{S} \cdot \tilde{a}_1 =$$

$$\frac{1}{p-1} \cdot \tilde{a}_1^T \cdot \left( \sum_{i=1}^{p} \cdot \tilde{y}_i \cdot \tilde{y}_i^T \right) \cdot \tilde{a}_1 = \frac{1}{p-1} \cdot \tilde{a}_1^T \cdot \left( \sum_{i=1}^{p} (\tilde{x}_i - \overline{x}) \cdot (\tilde{x}_i - \overline{x})^T \right) \cdot \tilde{a}_1$$

$(\tilde{x}_i - \overline{x})$ is the deviation of the time vs. enhancement curve (TEC) from the $i^{th}$ pixel (pixel block) from the mean of TECs from all pixels (pixel blocks). Thus, the eigenvectors: $\tilde{a}_1, \tilde{a}_2, \tilde{a}_3, \tilde{a}_4, \ldots, \tilde{a}_n$ represent the first, second, third, fourth, ..., and least dominant time vs. enhancement behaviour in the set of TECs from all pixels. The loadings of the eigenvectors $\tilde{a}_1, \tilde{a}_2, \tilde{a}_3, \tilde{a}_4, \ldots, \tilde{a}_n$ in the TEC from the $i^{th}$ pixel (pixel block) are:

$\tilde{a}_1^T \cdot \tilde{y}_i, \tilde{a}_2^T \cdot \tilde{y}_i, \tilde{a}_3^T \cdot \tilde{y}_i, \tilde{a}_4^T \cdot \tilde{y}_p, \ldots, \tilde{a}_n^T \cdot \tilde{y}_i$ and is the $i^{th}$ row of the matrix $\tilde{Z}$ while the loadings of the eigenvector $\tilde{a}_i$ in the TECs from all pixels (pixel blocks) are:

$$\tilde{a}_i^T \cdot \tilde{y}_1, \tilde{a}_i^T \cdot \tilde{y}_2, \tilde{a}_i^T \cdot \tilde{y}_3, \tilde{a}_i^T \cdot \tilde{y}_4, \ldots, \tilde{a}_i^T \cdot \tilde{y}_p$$

and is the $i^{th}$ column of the matrix $\tilde{Z}$. The $i^{th}$ column of $\tilde{Z}$, therefore, gives the loading map of the eigenvector $\tilde{a}_i$ which corresponds to the $i^{th}$ largest eigenvalue $\lambda_i$.

To de-noise the dynamic images from a CT Perfusion study, the reverse of the calculation of the loading maps of eigenvectors is required. Reconstituting a smooth version of the original dynamic images, $\tilde{Y}(\tilde{X})$, from a truncated series of eigenvectors $\tilde{a}_1, \tilde{a}_2, \tilde{a}_3, \tilde{a}_4, \ldots, \tilde{a}_r$ is necessary.

As in Equation (1), the p×n matrix $\tilde{Y}$ can be expanded by singular value decomposition as:

$$\tilde{Y} = \tilde{U} \cdot \tilde{L} \cdot \tilde{V}^T$$

where $\tilde{U}$ is a p×p orthogonal matrix, $\tilde{V}$ is a n×n orthogonal matrix, and $\tilde{L}$ is a p×n diagonal matrix with singular values of $\tilde{Y}$ as its diagonal elements. Let $l_1, \ldots, l_n$ be the singular values of $\tilde{Y}$ (it is assumed without loss of generality that $\tilde{Y}$ is of full column rank, n and p>n). Using the singular value decomposition:

$$\tilde{S} = \frac{1}{p-1} \cdot \tilde{Y}^T \cdot \tilde{Y}$$

$$= \frac{1}{p-1} \cdot (\tilde{U} \cdot \tilde{L} \cdot \tilde{V}^T)^T \cdot \tilde{U} \cdot \tilde{L} \cdot \tilde{V}^T$$

$$= \frac{1}{p-1} \cdot \tilde{V} \cdot \tilde{L}^T \cdot \tilde{U}^T \cdot \tilde{U} \cdot \tilde{L} \cdot \tilde{V}^T$$

$$= \frac{1}{p-1} \cdot \tilde{V} \cdot \tilde{L}^T \cdot \tilde{L} \cdot \tilde{V}^T$$

Multiplying both sides of the equation by $\tilde{V}$ yields:

$$\tilde{S} \cdot \tilde{V} = \frac{1}{p-1} \cdot \tilde{V} \cdot \tilde{L}^T \cdot \tilde{L} \tag{5}$$

$\tilde{L} = [\tilde{l}_1 \ldots \tilde{l}_i \ldots \tilde{l}_n]$ where $\tilde{l}_i$ $i=1, \ldots, n$ is a p×1 vector whose elements are all zero except the $i^{th}$ element which is equal to $l_i$, that is $\tilde{l}_i^T = [0 \ldots l_i \ldots 0]$ and $$\tilde{l}_i^T \cdot \tilde{l}_j = \begin{cases} l_i^2 & i=j \\ 0 & i \neq j \end{cases}$$

Then, $\tilde{L}^T \cdot \tilde{L} = \begin{bmatrix} \tilde{l}_1^T \\ \vdots \\ \tilde{l}_i^T \\ \vdots \\ \tilde{l}_n^T \end{bmatrix} \cdot [\tilde{l}_1 \ldots \tilde{l}_i \ldots \tilde{l}_n] = \begin{bmatrix} \tilde{m}_1^T \\ \vdots \\ \tilde{m}_i^T \\ \vdots \\ \tilde{m}_n^T \end{bmatrix}$ where $\tilde{m}_i^T = [0 \ldots l_i^2 \ldots 0]$.

Let $\tilde{V} = [\tilde{v}_1 \ldots \tilde{v}_i \ldots \tilde{v}_n]$ where $\tilde{v}_i$ $i=1, \ldots, n$ is a n×1 vector.

Then, $$\tilde{V} \cdot \tilde{L}^T \cdot \tilde{L} = [\tilde{v}_1 \ldots \tilde{v}_i \ldots \tilde{v}_n] \cdot \begin{bmatrix} \tilde{m}_1^T \\ \vdots \\ \tilde{m}_i^T \\ \vdots \\ \tilde{m}_n^T \end{bmatrix} = \sum_{i=1}^{n} \tilde{v}_i \cdot \tilde{m}_i^T = \sum_{i=1}^{n} \tilde{v}_i \cdot [0 \ldots l_i^2 \ldots 0] =$$

$$\sum_{i=1}^{n} [0 \ldots l_i^2 \cdot \tilde{v}_i \ldots 0] = [l_1^2 \cdot \tilde{v}_1 \ldots l_i^2 \cdot \tilde{v}_i \ldots l_n^2 \cdot \tilde{v}_n]$$

Substituting in Equation (5) yields:

$$\tilde{S} \cdot \tilde{V} = \frac{1}{p-1} \cdot \tilde{V} \cdot \tilde{L}^T \cdot \tilde{L} = \left[ \frac{l_1^2 \cdot \tilde{v}_1}{p-1} \ldots \frac{l_i^2 \cdot \tilde{v}_i}{p-1} \ldots \frac{l_n^2 \cdot \tilde{v}_n}{p-1} \right]$$

$$\Rightarrow [\tilde{S} \cdot \tilde{v}_1 \ldots \tilde{S} \cdot \tilde{v}_i \ldots \tilde{S} \cdot \tilde{v}_n] = \left[ \frac{l_1^2 \cdot \tilde{v}_1}{p-1} \ldots \frac{l_i^2 \cdot \tilde{v}_i}{p-1} \ldots \frac{l_n^2 \cdot \tilde{v}_n}{p-1} \right]$$

$$\Rightarrow \tilde{S} \cdot \tilde{v}_1 = \frac{l_i^2}{p-1} \cdot \tilde{v}_i \quad i=1, \ldots, n$$

From the discussion on eigenvectors and eigenvalues:

$$\tilde{v}_i = \tilde{a}_i \Rightarrow \tilde{V} = \tilde{A}$$

$$\frac{l_i^2}{p-1} = \lambda_i$$

or the singular values of $\tilde{Y}(l_i)$ is equal to the square root of (p−1) times the eigenvalue value of $\tilde{S}(\lambda_i)$, where $$\tilde{S} = \frac{1}{p-1} \cdot \tilde{Y}^T \cdot \tilde{Y},$$

i.e. $l_i = \sqrt{(p-1) \cdot \lambda_i}$

Thus, $$\tilde{Y}^T \cdot \tilde{Y} \cdot \tilde{v}_i = l_i^2 \cdot \tilde{v}_i \text{ or } \tilde{Y}^T \cdot \tilde{Y} \cdot \tilde{a}_i = l_i^2 \cdot \tilde{a}_i \quad i=1, \ldots, n \tag{5a}$$

Next, consider $$\tilde{S}^* = \frac{1}{p-1} \cdot \tilde{Y} \cdot \tilde{Y}^T \tag{6}$$

$$= \frac{1}{p-1} \cdot \tilde{U} \cdot \tilde{L} \cdot \tilde{V}^T \cdot (\tilde{U} \cdot \tilde{L} \cdot \tilde{V}^T)^T$$

$$= \frac{1}{p-1} \tilde{U} \cdot \tilde{L} \cdot \tilde{V}^T \cdot \tilde{V} \cdot \tilde{L}^T \cdot \tilde{U}^T$$

$$= \frac{1}{p-1} \tilde{U} \cdot L \cdot \tilde{L}^T \cdot \tilde{U}^T$$

(note that $\tilde{S}^*$ is not the transpose of $\tilde{S}$)

Multiplying both sides of the equation by $\tilde{U}$ yields:

$$\tilde{S}^* \cdot \tilde{U} = \frac{1}{p-1} \cdot \tilde{U} \cdot \tilde{L} \cdot \tilde{L}^T$$

-continued $$\tilde{L} \cdot \tilde{L}^T = [\tilde{1}_1 \ldots \tilde{1}_i \ldots \tilde{1}_n] \cdot \begin{bmatrix} \tilde{1}_1^T \\ \vdots \\ \tilde{1}_i^T \\ \vdots \\ \tilde{1}_n^T \end{bmatrix} = \sum_{i=1}^{n} \tilde{1}_i \cdot \tilde{1}_i^T$$

$$\tilde{1}_1 \cdot \tilde{1}_i^T = \begin{bmatrix} 0_1 \\ \vdots \\ 1_i \\ \vdots \\ 0_p \end{bmatrix}_{p \times 1} \cdot \underbrace{[0_1 \ldots 1_i \ldots 0_p]}_{1 \times p} = \begin{bmatrix} 0 & \ldots & 0_i & \ldots & 0_{1n} & \ldots & 0_{1p} \\ \vdots & \ddots & \vdots & \ddots & \vdots & \ddots & \vdots \\ 0_{i1} & \ldots & 1_i^2 & \ldots & 0_{in} & \ldots & 0_{ip} \\ \vdots & \ddots & \vdots & \ddots & \vdots & \ddots & \vdots \\ 0_{n1} & \ldots & 0_{ni} & \ldots & 0_{nn} & \ldots & 0_{np} \\ \vdots & \ddots & \vdots & \ddots & \vdots & \ddots & \vdots \\ 0_{p1} & \ldots & 0_{pi} & \ldots & 0_{pn} & \ldots & 0_{pp} \end{bmatrix}$$

$$\tilde{1}_i \cdot \tilde{1}_j^T = \begin{bmatrix} 0_1 \\ \vdots \\ 1_i \\ \vdots \\ 0_j \\ \vdots \\ 0_p \end{bmatrix}_{p \times 1} \cdot \underbrace{[0_1 \ldots 0_i \ldots 1_j \ldots 0_p]}_{1 \times p} = \tilde{0}_{p \times p}$$

Thus, $$\tilde{L} \cdot \tilde{L}^T = \begin{bmatrix} 1_1^2 & \ldots & 0_i & \ldots & 0_{1n} & \ldots & 0_{1p} \\ \vdots & \ddots & \vdots & \ddots & \vdots & \ddots & \vdots \\ 0_{i1} & \ldots & 1_i^2 & \ldots & 0_{in} & \ldots & 0_{ip} \\ \vdots & \ddots & \vdots & \ddots & \vdots & \ddots & \vdots \\ 0_{n1} & \ldots & 0_{ni} & \ldots & 1_n^2 & \ldots & 0_{np} \\ \vdots & \ddots & \vdots & \ddots & \vdots & \ddots & \vdots \\ 0_{p1} & \ldots & 0_{pi} & \ldots & 0_{pn} & \ldots & 0_{pp} \end{bmatrix} \begin{bmatrix} \tilde{m}_1^{*T} \\ \vdots \\ \tilde{m}_i^{*T} \\ \vdots \\ \tilde{m}_n^{*T} \\ \vdots \\ 0 \end{bmatrix}$$

Let $\tilde{m}_i^* = [0 \ldots 1_i^2 \ldots 0_p]^T$ be a p×1 vector as defined, then $$\tilde{L} \cdot \tilde{L}^T = \begin{bmatrix} \tilde{m}_1^{*T} \\ \vdots \\ \tilde{m}_i^{*T} \\ \vdots \\ \tilde{m}_n^{*T} \\ 0_{n+1} \\ \vdots \\ 0_p \end{bmatrix}$$

Let $\tilde{U} = [\tilde{u}_1 \ldots \tilde{u}_i \ldots \tilde{u}_p]$ where $\tilde{u}_i$, $i=1, \ldots, p$ is a p×1 vector.

Then, $$\tilde{U} \cdot \tilde{L} \cdot \tilde{L}^T = [\tilde{u}_1 \ldots \tilde{u}_i \ldots \tilde{u}_n \, \tilde{u}_{n+1} \ldots \tilde{u}_p] \cdot \begin{bmatrix} \tilde{m}_1^{*T} \\ \vdots \\ \tilde{m}_i^{*T} \\ \vdots \\ \tilde{m}_n^{*T} \\ 0_{n+1} \\ \vdots \\ 0_p \end{bmatrix}$$

$$= \sum_{i=1}^{n} \tilde{u}_i \cdot \tilde{m}_i^T 1$$

$$= \sum_{i=1}^{n} \tilde{u}_i \cdot [0 \ldots 1_i^2 \ldots 0_p] + \sum_{i=n+1}^{p} \tilde{u}_i \cdot [0 \ldots 0_i \ldots 0_p]$$

$$= \sum_{i=1}^{n} [0 \ldots 1_i^2 \cdot \tilde{u}_i \ldots 0_p]$$

$$= [1_1^2 \cdot \tilde{u}_1 \ldots 1_i^2 \cdot \tilde{u}_i \ldots 1_n^2 \cdot \tilde{u}_n \, 0_{n+1} \ldots 0_p]$$

Substituting in Equation (6) yields:

$$\tilde{S}^* \cdot \tilde{U} = \frac{1}{p-1} \cdot \tilde{U} \cdot \tilde{L} \cdot \tilde{L}^T = \left[ \frac{1_1^2 \cdot \tilde{u}_1}{p-1} \ldots \frac{1_i^2 \cdot \tilde{u}_i}{p-1} \ldots \frac{1_n^2 \cdot \tilde{u}_n}{p-1} \, 0_{n+1} \ldots 0_p \right]$$

$$\Rightarrow [\tilde{S}^* \cdot \tilde{u}_i \ldots \tilde{S}^* \cdot \tilde{u}_i \ldots \tilde{S}^* \cdot \tilde{u}_n \, 0_{n+1} \ldots 0_p] =$$

$$\left[ \frac{1_1^2 \cdot \tilde{u}_1}{p-1} \ldots \frac{1_i^2 \cdot \tilde{u}_i}{p-1} \ldots \frac{1_n^2 \cdot \tilde{u}_n}{p-1} \, 0_{n+1} \right]$$

$$\Rightarrow \tilde{S}^* \cdot \tilde{u}_i = \begin{cases} \frac{1_i^2}{p-1} \cdot \tilde{u}_i & i \leq n \\ 0 \cdot \tilde{u}_i & n+1 \leq i \leq p \end{cases}$$

Thus, $\tilde{u}_i$, $i=1, \ldots, n$ is the eigenvector of $\tilde{S}^*$ corresponding to the $i^{th}$ eigenvalue $$\frac{1_i^2}{p-1},$$

which happens also to be the $i^{th}$ eigenvalue of $\tilde{S}$, while all $\tilde{u}_i$ $i=n+1, \ldots, p$ are eigenvectors of $\tilde{S}^*$ with zero eigenvalue. Also $$\tilde{Y} \cdot \tilde{Y}^T \cdot \tilde{u}_i = l_i^2 \cdot \tilde{u}_i \quad i=1, \ldots, n \quad (6a)$$

As stated above, Equation (5a) is:

$$\tilde{Y}^T \cdot \tilde{Y} \cdot \tilde{v}_i = l_i^2 \cdot \tilde{v}_i$$

Multiplying both sides by $\tilde{Y}$ yields:

$$\tilde{Y} \cdot \tilde{Y}^T \cdot \tilde{Y} \cdot \tilde{v}_i = l_i^2 \cdot \tilde{Y} \cdot \tilde{v}_i$$

Comparing with Equation (6a):

$$\tilde{Y} \cdot \tilde{v}_i = c \cdot \tilde{u}_i \text{ where } c \text{ is a constant} \quad (7a)$$

Similarly multiplying both sides of Equation (6a) by $\tilde{Y}^T$ yields:

$$\tilde{Y}^T \cdot \tilde{Y} \cdot \tilde{Y}^T \cdot \tilde{u}_i = l_i^2 \cdot \tilde{Y}^T \cdot \tilde{u}_i$$

Comparing with Equation (5a):

$$\tilde{Y}^T \cdot \tilde{u}_i = c^* \cdot \tilde{v}_i \text{ where } c \text{ is a constant} \quad (7b)$$

From Equation (7b):

$$\tilde{v}_i = \frac{1}{c^*} \cdot \tilde{Y}^T \cdot \tilde{u}_i$$

Substituting into Equation (7a) yields:

$$\tilde{Y} \cdot \tilde{Y}^T \cdot \tilde{u}_i = c^* \cdot c \cdot \tilde{u}_i$$

Substituting into Equation (6a) yields:

$$l_i^2 \cdot \tilde{u}_i = c^* \cdot c \cdot \tilde{u}_i$$

Therefore, $c^* \cdot c = l_i^2$
Without loss of generality, $c^*$ is set to:

$$c^* = c = l_i = \sqrt{(p-1) \cdot \lambda_i} \; i = 1, \ldots, n \text{ and } n < p$$

Thus, for the singular value decomposition of $\tilde{Y}$:

$$\tilde{Y} = \tilde{U} \cdot \tilde{L} \cdot \tilde{V}^T$$

where $\tilde{U}$ is a p×p orthogonal matrix:

$$\tilde{U} = [\tilde{u}_1 \ldots \tilde{u}_i \ldots \tilde{u}_p] \text{ and } \tilde{u}_i \, i=1, \ldots, p \text{ is a } p \times 1 \text{ vector};$$

$\tilde{V}$ is a n×n orthogonal matrix:

$$\tilde{V} = [\tilde{v}_1 \ldots \tilde{v}_i \ldots \tilde{v}_n] \text{ and } \tilde{v}_i \, i=1, \ldots, n \text{ is a } n \times 1 \text{ vector};$$

and $\tilde{L}$ is a p×n diagonal matrix with singular values of $\tilde{Y}$, $1_1, \ldots, 1_n$, as its diagonal elements; it is also assumed without loss of generality that $\tilde{Y}$ is of full column rank, n and p>n.
It is shown that:
$\tilde{v}_i = \tilde{a}_i$ where $\tilde{a}_i$ is the $i^{th}$ eigenvector of $$\tilde{S} = \frac{1}{p-1} \cdot \tilde{Y}^T \cdot \tilde{Y}$$

corresponding to the eigenvalue $$\frac{1_i^2}{(p-1)};$$

and from Equation (7c)

$$\tilde{u}_i = \frac{1}{c} \tilde{Y} \cdot \tilde{v}_i = \frac{1}{\sqrt{(p-1) \cdot \lambda_i}} \cdot \tilde{Y} \cdot \tilde{a}_i$$

As discussed above, to de-noise $\tilde{Y}$ the SVD expansion can be truncated after the $r^{th}$ singular value:

$$\tilde{Y} \approx \sum_{i=1}^{r} 1_i \cdot \tilde{u}_i \cdot \tilde{v}_i^T = \sum_{i=1}^{r} 1_i \cdot \tilde{u}_i \cdot \tilde{a}_i^T = \sum_{i=1}^{r} 1_i \cdot \frac{1}{\sqrt{(p-1) \cdot \lambda_i}} \cdot \tilde{Y} \cdot \tilde{a}_i \cdot \tilde{a}_i^T = \quad (8)$$

$$\sum_{i=1}^{r} \tilde{Y} \cdot \tilde{a}_i \cdot \tilde{a}_i^T \Longrightarrow \tilde{Y} \approx \tilde{Y} \cdot \sum_{i=1}^{r} \tilde{a}_i \cdot \tilde{a}_i^T$$

Equation (8) also affords a very simple geometric interpretation as explained in the following.

$$\tilde{Y} \approx \tilde{Y} \cdot \sum_{i=1}^{r} \tilde{a}_i \cdot \tilde{a}_i^T = \quad (9)$$

$$\sum_{i=1}^{r} \tilde{Y} \cdot \tilde{a}_i \cdot \tilde{a}_i^T = (\tilde{Y} \cdot \tilde{a}_1 \; \tilde{Y} \cdot \tilde{a}_2 \; \ldots \; \tilde{Y} \cdot \tilde{a}_{r-1} \; \tilde{Y} \cdot \tilde{a}_r) \cdot \begin{pmatrix} \tilde{a}_1^T \\ \tilde{a}_2^T \\ \vdots \\ \tilde{a}_{r-1}^T \\ \tilde{a}_r^T \end{pmatrix} = \tilde{Y} \cdot \tilde{A}_r \cdot \tilde{A}_r^T$$

where $\tilde{A}_r$ is a n×r matrix whose $i^{th}$ column is $\tilde{a}_i$ and from Equation (4a):

$$\tilde{Z}_r = \tilde{Y} \cdot \tilde{A}_r$$

and the rows and columns of $\tilde{Z}_r$ have the same interpretation as those of $\tilde{Z}$.

Rewrite Equation (9):

$$\tilde{Y} \approx \tilde{Y} \cdot \sum_{i=1}^{r} \tilde{a}_i \cdot \tilde{a}_i^T = \quad (10)$$

$$\sum_{i=1}^{r} \tilde{Y} \cdot \tilde{a}_i \cdot \tilde{a}_i^T = (\tilde{Y} \cdot \tilde{a}_1 \; \tilde{Y} \cdot \tilde{a}_2 \; \ldots \; \tilde{Y} \cdot \tilde{a}_{r-1} \; \tilde{Y} \cdot \tilde{a}_r) \cdot \begin{pmatrix} \tilde{a}_1^T \\ \tilde{a}_2^T \\ \vdots \\ \tilde{a}_{r-1}^T \\ \tilde{a}_r^T \end{pmatrix} =$$

$$\left( \begin{pmatrix} \tilde{y}_1^T \\ \tilde{y}_2^T \\ \vdots \\ \tilde{y}_{p-1}^T \\ \tilde{y}_p^T \end{pmatrix} \cdot \tilde{a}_1 \; \begin{pmatrix} \tilde{y}_1^T \\ \tilde{y}_2^T \\ \vdots \\ \tilde{y}_{p-1}^T \\ \tilde{y}_p^T \end{pmatrix} \cdot \tilde{a}_2 \; \ldots \; \begin{pmatrix} \tilde{y}_1^T \\ \tilde{y}_2^T \\ \vdots \\ \tilde{y}_{p-1}^T \\ \tilde{y}_p^T \end{pmatrix} \cdot \tilde{a}_{r-1} \; \begin{pmatrix} \tilde{y}_1^T \\ \tilde{y}_2^T \\ \vdots \\ \tilde{y}_{p-1}^T \\ \tilde{y}_p^T \end{pmatrix} \cdot \tilde{a}_r \right) \cdot \begin{pmatrix} \tilde{a}_1^T \\ \tilde{a}_2^T \\ \vdots \\ \tilde{a}_{r-1}^T \\ \tilde{a}_r^T \end{pmatrix} =$$

$$\begin{pmatrix} \tilde{y}_1^T \cdot \tilde{a}_1 & \tilde{y}_1^T \cdot \tilde{a}_2 & \ldots & \tilde{y}_1^T \cdot \tilde{a}_{r-1} & \tilde{y}_1^T \cdot \tilde{a}_r \\ \tilde{y}_2^T \cdot \tilde{a}_1 & \tilde{y}_2^T \cdot \tilde{a}_2 & \ldots & \tilde{z}_2^T \cdot \tilde{a}_{r-1} & \tilde{z}_2^T \cdot \tilde{a}_r \\ \vdots & \vdots & \ldots & \vdots & \vdots \\ \tilde{y}_{p-1}^T \cdot \tilde{a}_1 & \tilde{y}_{p-1}^T \cdot \tilde{a}_2 & \ldots & \tilde{y}_{p-1}^T \cdot \tilde{a}_{r-1} & \tilde{y}_{p-1}^T \cdot \tilde{a}_r \\ \tilde{y}_p^T \cdot \tilde{a}_1 & \tilde{y}_p^T \cdot \tilde{a}_2 & \ldots & \tilde{y}_p^T \cdot \tilde{a}_{r-1} & \tilde{y}_p^T \cdot \tilde{a}_r \end{pmatrix} \cdot \begin{pmatrix} \tilde{a}_1^T \\ \tilde{a}_2^T \\ \vdots \\ \tilde{a}_{r-1}^T \\ \tilde{a}_r^T \end{pmatrix} =$$

$$\begin{pmatrix} \sum_{i=1}^{r} (\tilde{y}_1^T \cdot \tilde{a}_i) \cdot \tilde{a}_i^T \\ \sum_{i=1}^{r} (\tilde{y}_2^T \cdot \tilde{a}_i) \cdot \tilde{a}_i^T \\ \vdots \\ \sum_{i=1}^{r} (\tilde{y}_{p-1}^T \cdot \tilde{a}_i) \cdot \tilde{a}_i^T \\ \sum_{i=1}^{r} (\tilde{y}_p^T \cdot \tilde{a}_i) \cdot \tilde{a}_i^T \end{pmatrix}$$

Equation (10) suggests that the TEC for the $i^{th}$ pixel (pixel block) is a weighted summation of r eigenvectors with the weights given by the loading of the $i^{th}$ pixel TEC on the eigenvectors.

The eigenvectors $\tilde{a}_1, \tilde{a}_2, \ldots, \tilde{a}_{r-1}, \tilde{a}_r$ can be regarded as forming an orthonormal basis in n dimensional space. The projection of $\tilde{y}_i$ on $\tilde{a}_i$ is $\tilde{y}_i^T \cdot \tilde{a}_i$ and $\tilde{y}_i$ can be reconstituted as $$\sum_{j=1}^{r} (\tilde{y}_i^T \cdot \tilde{a}_j) \cdot \tilde{a}_j^T.$$

The algorithm to de-noise $\tilde{X} = [\tilde{x}_1^T \ldots \tilde{x}_i^T \ldots \tilde{x}_p^T]$ is as follows:

1. Calculate the p×n zero mean matrix, $\tilde{Y} = [\tilde{y}_1^T \ldots \tilde{y}_i^T \ldots \tilde{y}_p^T]^T$, corresponding to $\tilde{X}$, where $$\tilde{y}_i = \tilde{x}_i - \bar{x} \text{ and } \bar{x} = \frac{1}{p} \cdot \sum_{i=1}^{p} \tilde{x}_i$$

2. Calculate the n×n sample covariance matrix, $\tilde{S}$:

$$\tilde{S} = \frac{1}{p-1} \cdot \tilde{Y}^T \cdot \tilde{Y}$$

3. Calculate the n pairs of eigenvalue and eigenvectors, $$(\lambda_i, \tilde{a}_i) i = 1, \ldots, n$$

4. Calculate the n×n smoothing matrix by keeping only the largest r eigenvalues:

$$\sum_{i=1}^{r} \tilde{a}_i \cdot \tilde{a}_i^T$$

5. Smooth $\tilde{Y} = [\tilde{y}_1 \ldots \tilde{y}_i \ldots \tilde{y}_p]$ by calculating the product:

$$\tilde{Y}^* = [\tilde{y}_1^* \ldots \tilde{y}_i^* \ldots \tilde{y}_p^*] \approx \tilde{Y} \cdot \sum_{i=1}^{r} \tilde{a}_i \cdot \tilde{a}_i^T$$

6. Calculate a smoothed version of $\tilde{X}^*$ as follows:

$$\tilde{X}^* = [\tilde{y}_1^* + \bar{x} \ldots \tilde{y}_i^* + \bar{x} \ldots \tilde{y}_p^* + \bar{x}].$$

An example of the method described herein will now be demonstrated with regard to experimental results. The principal component analysis (PCA) described herein is tested for the ability to achieve dose reduction of CT scans.

The PCA method will now be summarized based on a CT Perfusion study that generates a plurality of time separated images that capture the passage of contrast through the brain. Corresponding to each pixel in the series of images, a curve is generated that represents the contrast concentration in that pixel as a function of time. A difference curve, equal to the difference of the curve from the mean of all pixel curves is also generated. A covariance matrix of the co-variations of all pairs of difference curves is calculated and represents all possible variations about the mean curve. The principal component analysis method analyzes the covariance matrix to find common temporal patterns among the curves by finding linear combinations of the difference curves that represent most of the variations about the mean curve. It can be shown that such linear combinations, or principal components, are the eigenvectors of the covariance matrix and that the eigenvector with the largest eigenvalue is the most prominent temporal feature among all the difference curves, the eigenvector with the second largest eigenvalue is the second most prominent temporal feature and so on, while eigenvectors with small eigenvalues are from noise in the CT images. A corollary is that each difference curve can be represented as a sum of all the principal components and by discarding components with small eigenvalues, noise can be effectively suppressed. To denoise the time series of images, the mean curve is added to all the difference curves reconstituted by using the first few principal components with large eigenvalues.

While currently available statistical filters remove noise in projection data before image reconstruction, the principal component analysis method removes noise from the reconstructed images. Experimental results described below show that performing PCA leads to dose reduction in CT imaging.

The PCA method is tested versus the traditional filtered back-projection (FBP) method in radiation dose reduction for CT Perfusion applications. The dose saving of PCA versus FBP on measuring brain perfusion using CT Perfusion was tested in a healthy pig, which was scanned four times with the x-ray tube current changed from 190 mA to 100 mA; 75 mA and 50 mA, respectively, while keeping other scanning parameters the same.

Figure 3:
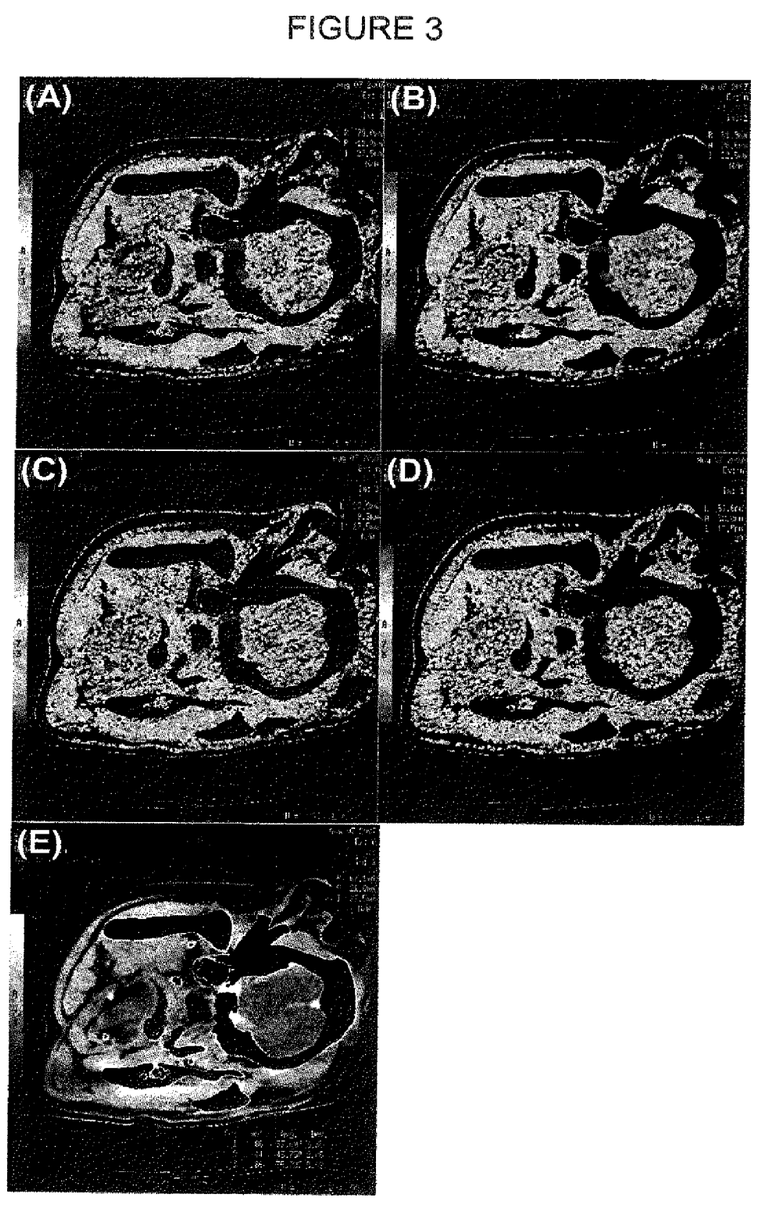
FIGS. 3A to 3E show brain blood flow maps from CT images processed with a statistical filtering technique.

FIG. 3 shows brain blood flow maps of the pig calculated using the J-W model with CT Perfusion images obtained using (A) 190 mA and FBP reconstruction; (B) 100 mA, FBP reconstruction and PCA; (C) 70 mA, FBP reconstruction and PCA; and, (D) 50 mA, FBP reconstruction and PCA. FIG. 3(E) shows regions of interest (3 outlined circles) used for calculation of Figure of Merit of the blood flow maps shown in FIG. 4. The regions are superimposed on a CT image which shows a coronal section through the brain of the pig. The dark areas are the skull and jaw bones.

Figure 4:
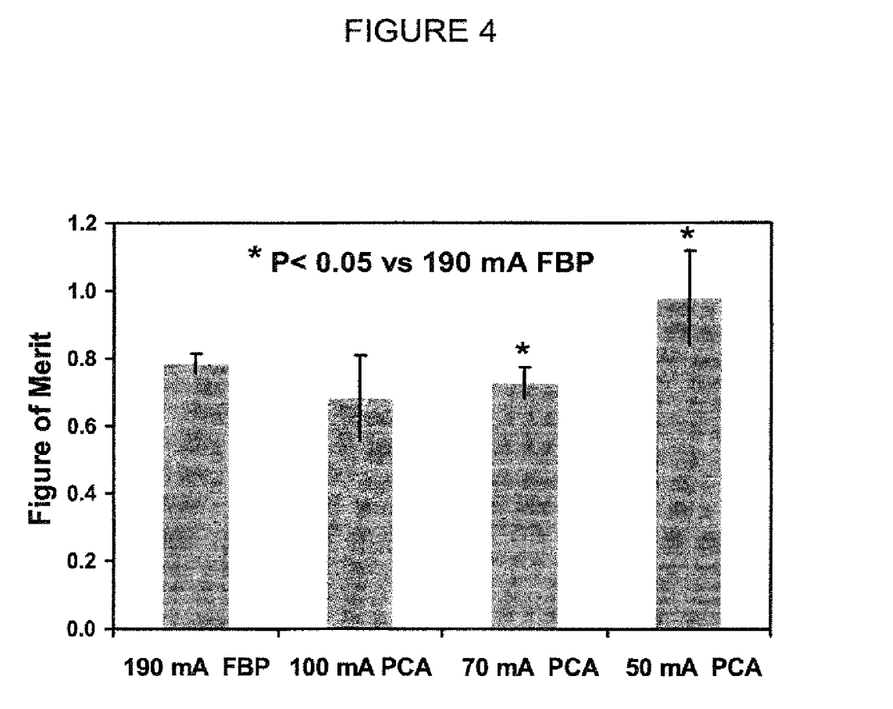
FIG. 4 graphically shows blood flow Figure of Merit calculated for the images shown in FIGS. 3A to 3D using the regions outlined in FIG. 3E.

FIG. 4 shows that in terms of standard deviation/mean of blood flow (Figure of Merit) in the three regions shown in FIG. 3(E): 70 mA with PCA was better than 190 mA with FBP, while 50 mA PCA was worse than 190 mA with FBP (p<0.05). The image quality of the blood flow maps in FIG. 3 also reflects this progression. Therefore, the PCA method is able to reduce radiation dose required to obtain images in CT Perfusion studies and in maintaining the quality of derived blood flow maps compared to the use of FBP alone. More specifically, the PCA method achieved approximately three fold reduction in radiation dose compared to the use of FBP alone. The effect of the PCA method on dose reduction in production of BBB-PS maps was not demonstrated because the blood-brain barrier remained intact. However, since blood flow, blood volume and BBB-PS are calculated together in the J-W model, the dose reduction shown using blood flow maps is expected to apply to BBB-PS maps.

The principal component analysis methodology described herein has been implemented in a computer executable software application using C++. The time required to process ninety-five (95) 512×512 CT brain images is less than two (2)

minutes on a general purpose computing device such as for example a personal computer (PC).

Figure 5:
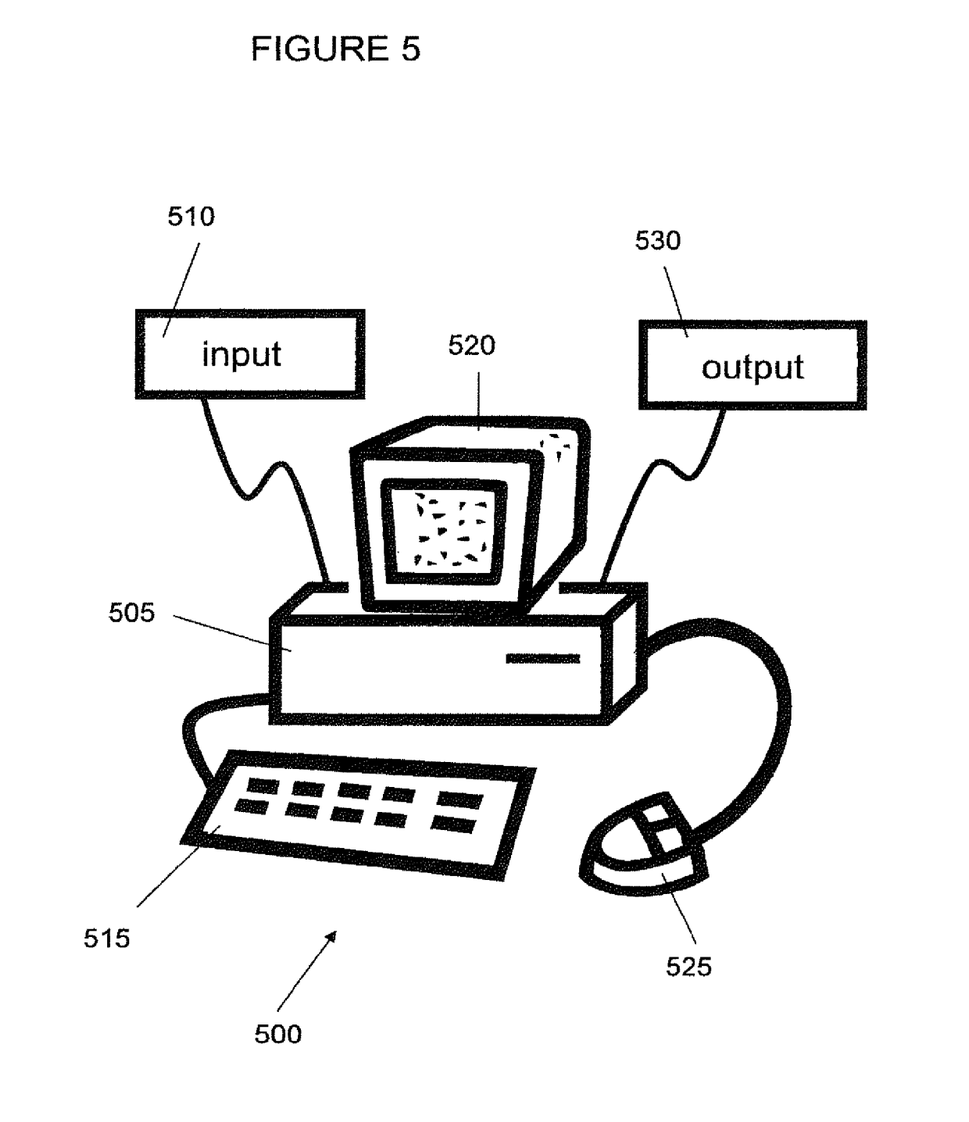
FIG. 5 is a diagram of a system for implementing the image processing method shown in FIG. 1.

The method described herein can be implemented on hardware such as system 400 shown in FIG. 5. An input 510 receives a plurality of time separated images, which can be previously stored, received directly from an imaging device, or communicated over a wired or wireless communication link from a remote location. A general purpose computing device 505 receives the time separated images from the input and executes a software application thereby to process the time separated images as described above. The general purpose computing device 505 interfaces with the user through a display 520, a keyboard 515 and/or a mouse or other pointing device 525. Results, for example the constructed processed images, can be presented on display 520 and/or output to any suitable output device 530, for example, a printer, a storage device, or a communication device for communicating the results to a remote location.

The software application described herein may run as a stand-alone application or may be incorporated into other available applications to provide enhanced functionality to those applications. The software application may include program modules including routines, programs, object components, data structures etc. and may be embodied as computer readable program code stored on a computer readable medium. The computer readable medium is any data storage device that can store data, which can thereafter be read by a computer system. Examples of computer readable media include for example read-only memory, random-access memory, CD-ROMs, magnetic tape and optical data storage devices. The computer readable program code can also be distributed over a network including coupled computer systems so that the computer readable program code is stored and executed in a distributed fashion.

The above-described embodiments are intended to be examples and alterations and modifications may be effected thereto, by those of skill in the art, without departing from the scope of the invention which is defined by the claims appended hereto.

What is claimed is:

1. A method of medical image processing comprising:
    capturing a plurality of time separated images of a target region of interest of a patient, wherein the plurality of time separated images capture a time-varying behavior of said target region of interest;
    selecting a plurality of imaging units from each of the plurality of captured time separated images, wherein the selected plurality of imaging units are at the same location within each of the plurality of captured time separated images;
    representing each of the selected plurality of imaging units by a value;
    for each imaging unit location, using the corresponding values to determine a temporal difference for the selected imaging units;
    selecting temporal differences above a threshold limit; and
    constructing a noise reduced image based on the selected temporal differences.

2. The method of claim 1, further comprising ranking each measured temporal difference prior to said selecting.

3. The method of claim 1, wherein each imaging unit is one of a pixel and a voxel.

4. The method of claim 1, wherein each imaging unit is one of a plurality of pixels and a plurality of voxels.

5. The method of claim 1, wherein the temporal difference is based on contrast enhancement.

6. The method of claim 5, wherein the temporal difference is a difference of a contrast agent.

7. The method of claim 6, wherein contrast enhancement is based on the concentration of the contrast agent.

8. The method of claim 6, wherein contrast enhancement is based on the activation of the contrast agent.

9. The method of claim 1, further comprising characterizing the measured temporal differences with a blind signal separation statistical technique.

10. The method of claim 1, wherein determining the temporal difference comprises calculating a covariance matrix of temporal differences for the imaging units.

11. The method of claim 10, further comprising analyzing the covariance matrix with a blind signal separation statistical technique to determine common temporal patterns among the temporal differences.

12. The method of claim 11, further comprising analyzing the eigenvectors of the covariance matrix.

13. The method of claim 12, wherein eigenvalues of the eigenvector represent the degree of temporal difference.

14. The method of claim 13, wherein the selecting of temporal differences comprises selecting eigenvalues above the threshold limit.

15. The method of claim 1, wherein the threshold limit is adjustable.

16. The method of claim 11, wherein the blind signal separation statistical technique is selected from the group consisting of principal component analysis, independent component analysis, blind source deconvolution, Karhunen-Loeve transform and Hotelling transform.

17. The method of claim 1, wherein the plurality of time separated images are captured using a dynamic medical imaging technique.

18. The method of claim 17, wherein the dynamic medical imaging technique comprises use of a contrast agent.

19. The method of claim 17, wherein the time separated images are captured using a dynamic medical imaging technique that employs a protocol having a reduced radiation dose.

20. The method of claim 17, wherein the time separated images are captured using a dynamic medical imaging technique that employs a protocol having a reduced amount of contrast agent.

21. The method of claim 17, wherein the dynamic medical imaging technique is magnetic resonance imaging (MRI), functional MRI, positron emission tomography, nuclear medicine or computed tomography.

22. The method of claim 17, wherein the dynamic medical imaging technique is computed tomography (CT).

23. The method of claim 22, wherein the time separated images are captured using a CT Perfusion protocol having a reduced radiation dose.

24. The method of claim 22, wherein the time separated images are captured using a CT Perfusion protocol having a reduced amount of contrast agent.

25. A system for medical image processing comprising:
    an interface configured to receive a plurality of captured time separated images of a target region of interest of a patient, wherein the plurality of captured time separated images show a time-varying behavior of said target region of interest; and
    a processing structure communicating with said interface and configured to process said plurality of captured time separated images, wherein during processing of said captured time separated images, said processing structure is configured to select a plurality of imaging units from each of the plurality of captured time separated images, wherein the selected imaging units are at the same locations in each of said plurality of captured time separated images, represent each of the selected imaging units by a value, for each imaging unit location, use the values representing the selected imaging units in each of the time separated images to determine a temporal difference for the selected imaging units, select temporal differences above a threshold limit, and construct a noised reduced image based on the selected temporal differences.

26. A non-transitory computer readable medium embodying a computer program for medical image processing, the computer program comprising computer program code, which when executed by one or more processors, causes an apparatus at least to:

capture a plurality of time separated images of a target region of interest of a patient, wherein the plurality of captured time separated images image a time-varying behavior of said target region of interest;

select a plurality of imaging units from each of the plurality of captured time separated images, wherein the selected imaging units are at the same locations in each of said captured images;

represent each of the selected imaging units by a value;

for each imaging unit location, use the values representing the selected imaging units in each of the time separated images to determine a temporal difference for the selected imaging units;

select temporal differences above a threshold limit; and construct a noise reduced image based on the selected temporal differences.

* * * * *